United States Patent [19]

DeCastro et al.

[11] Patent Number: 4,899,733

[45] Date of Patent: Feb. 13, 1990

[54] DEVICE AND TECHNIQUE FOR TRANSURETHRAL ULTRASONIC LITHOTRIPSY USING A FLEXIBLE URETEROSCOPE

[75] Inventors: Eugene A. DeCastro, Jamestown, N.Y.; Roger Goodfriend, Monte Serno, Calif.

[73] Assignee: Blackstone Ultrasonic, Inc., Jamestown, N.Y.

[21] Appl. No.: 286,561

[22] Filed: Dec. 19, 1988

[51] Int. Cl.$^4$ .............................................. A61B 1/30
[52] U.S. Cl. .................................... 128/7; 128/24 A; 606/128
[58] Field of Search .............. 128/7, 6, 328 R, 328 V, 128/24 A

[56] References Cited

U.S. PATENT DOCUMENTS

| 3,830,240 | 8/1974 | Antonevich et al. | 128/328 V |
| 4,800,870 | 1/1989 | Reid, Jr. | 128/6 |

FOREIGN PATENT DOCUMENTS

| 657331 | 1/1929 | France | 128/7 |

Primary Examiner—William H. Grieb
Attorney, Agent, or Firm—Charles L. Lovercheck; Wayne L. Lovercheck; Dale R. Lovercheck

[57] ABSTRACT

An apparatus and method for machining or disintegrating a calculi in place in a urinary tract. The apparatus includes a flexible, hollow endoscope which can be inserted into a ureter in its flexible state and a relatively rigid hollow tube which can be inserted into a passageway through the endoscope to straighten it. Optionally, a guide wire can be inserted in the ureter to the position of the calculi before inserting the endoscope for guiding the endoscope into the ureter. The passageway through the endoscope is larger than the rigid hollow tube. An optical system that may be made up of optical fibers can be received in and extend through the endoscope to view the calculi. A wave guide wire can be extended through the relatively rigid tube and connected to a transducer to disintegrate the calculi. The relatively rigid tube can be moved laterally in the endoscope to bring the wave guide into engagement with the calculi to facilitate disintegrating the calculi. An irrigation means can be connected to the hollow endoscope. The endoscope can have several passageways.

15 Claims, 2 Drawing Sheets

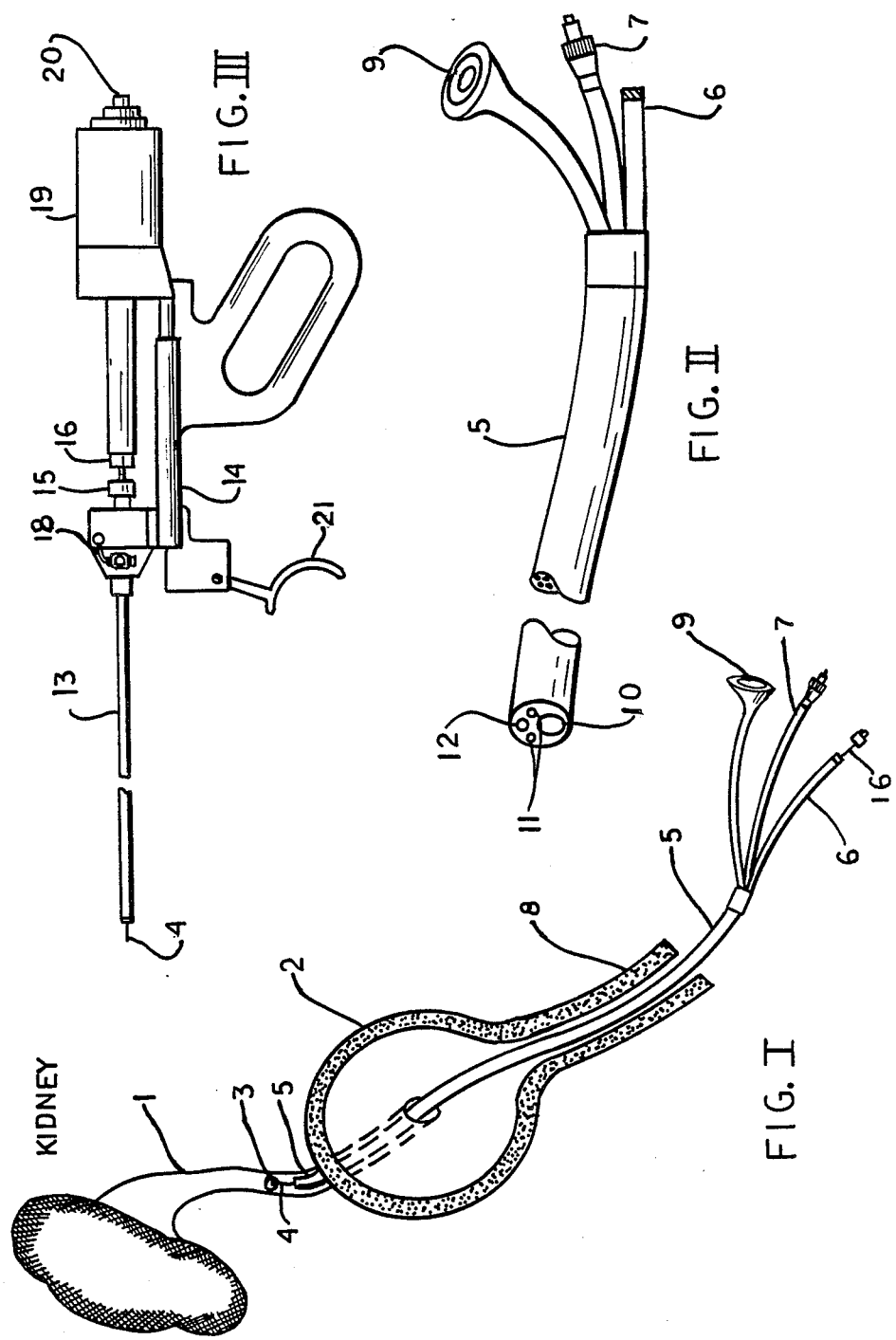

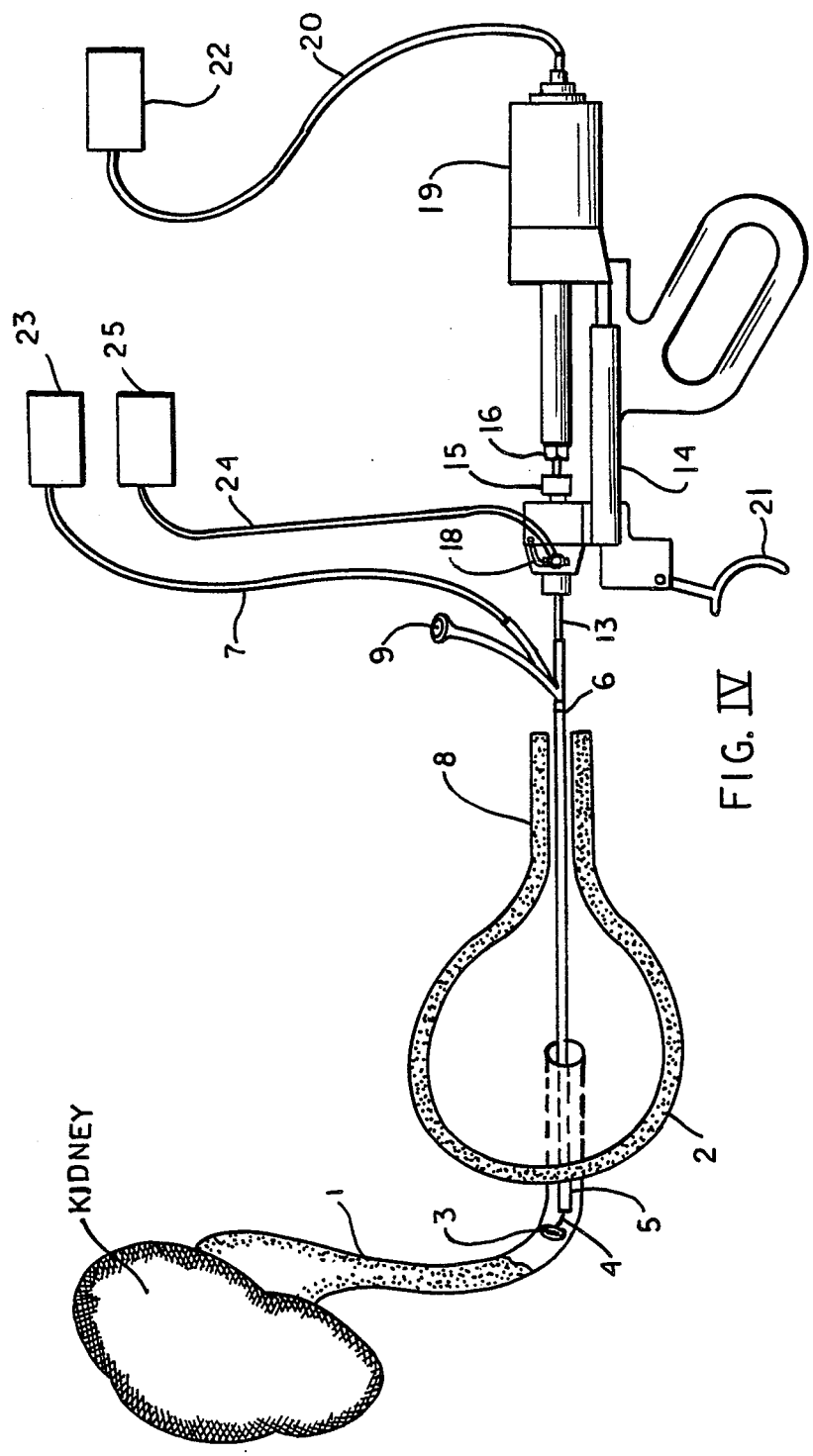
FIG. IV

DEVICE AND TECHNIQUE FOR TRANSURETHRAL ULTRASONIC LITHOTRIPSY USING A FLEXIBLE URETEROSCOPE

BACKGROUND OF INVENTION

The invention relates to the methods and apparatus for the disintegration of urinary calculi under direct vision and particularly to such methods or techniques using ultrasonic apparatus jointly with direct visual observation of the disintegration of the urinary calculus.

Vibration for the disintegration of urinary stones has been a popular maneuver. The jack hammer effect on these hard objects disintegrates calculi whereas the soft tissue underneath which is not rigidly fixed is relatively unaffected.

In U.S. Pat. No. 3,830,240 to Antonevich and Goodfriend proposed the use of an ultrasonic method and apparatus for the disintegration of stones. The apparatus and method of that patent involved inserting a catheter carrying a coupling member through the ureter until it abutted the stone and then subjected the coupling member to ultrasonic vibration with its free end against the stone to cause it to disintegrate the stone. A problem with this method and apparatus is the catheter is a rigid device and is difficult to introduce into and up the ureter.

Prior methods require a rigid ureteroscope to allow passage of rigid hollow tube wave guide used by some ultrasonic devices. The use of a rigid ureteroscope requires a high degree of operator skill in its use and not all practicing physicians have the opportunity or time to train at teaching institutions and many are timid in the use of a rigid instrument without such training.

We have found the urinary stones can be quickly fragmented and removed if a wave guide or coupling member is passed through the lumen of a flexible ureteroscope, that has been straightened after insertion into the ureter by a rigid or semi-rigid hollow tube, so that the wave guide or wire touches the stone to be fragmented and the relative size of the wave guide with respect to the hollow tube is such that lateral motion of the wave guide within the hollow tube is possible.

In the practice of the present invention, a flexible ureteroscope is inserted into the ureter using a guide wire that has been previously advanced to the position of the stone. The ureteroscope being flexible conforms easily to the natural contours and bends of the ureter as it is advanced. At this time the guide wire, if employed, is removed from the working guide wire may be in place beside the channel. A second safety guide wire may be in place beside the ureteroscope. Aided by the fiber optics system employed in the flexible ureteroscope the stone can be observed. A rigid or semi-rigid hollow tube is advanced through a lumen in the flexible ureteroscope, thus straightening the scope and ureter. Preferably a solid wire wave guide attached at the proximal end to an ultrasonic transducer is advanced through the hollow semi-rigid tube to the site of the stone. Under direct visual control of the physician, the distal end of the solid wave guide is abutted against the stone and irrigation through the tube initiated. The ultrasonic transducer is activated while the physician is observing the work of the solid wire machining the stone. Both transverse and longitudinal motion of the wire machine disintegrate the stone usually very quickly. The irrigation provides improved vision as well as cooling the wire.

The invention will be described with reference to the drawings which illustrate preferred surgical procedure that may be employed in practicing the invention. Other procedures for approaching the stone may be used. The invention is accordingly not to be construed as limited to the particular procedures shown. The present invention consists of the combination and arrangement of parts hereinafter more fully described, illustrated in the accompanying drawing and more particularly pointed out in the appended claims, it being proportions and minor detail of construction without departing from the spirit or sacrificing any of the advantages of the invention.

BRIEF DESCRIPTION OF THE DRAWINGS

FIG. I is a detailed view of the flexible ureteroscope shown in position in the flexible state.

FIG. II is a detailed view of the distal end of the flexible ureteroscope.

FIG. III is a detailed view of the rigid or semirigid tube attached to a handle assembly mounting the ultrasonic transducer and solid wire wave guide.

FIG. IV is a general view showing straightening of the ureteroscope and ureter after placing the semi-rigid tube in position.

In the preferred embodiments of the invention, refer to the drawings in detail on FIGS. I through IV. Referring to the drawings, we have illustrated flexible ureteroscope 5 with parallel lumens and one or more passageways 10, extending from one end to the other of ureteroscope 5. One lumen carries flexible optical system 12 which extends from one end of ureteroscope 5 which is inserted through urethra 8 and bladder 2 of a patient, into ureter 1 until it comes in contact with stone 3 to be disintegrated. The optical system consists of a means of conducting light 11 from a source 7 to illuminate stone 3 and lens system 12, which is connected to viewing means 9 through which the operating surgeon may view the area of stone 3 being machined. A wave guide, or coupling member, in the form of a solid wire 4, is inserted through lumen 10 of ureteroscope 5 until one end contacts stone 3. The other end extends out of the free end of ureteroscope 5 outside the patients' body and is attached to ultrasonic transducer 19, or a motor, by means of screw 16 attached or brazed to wave guide 4.

In the embodiment of FIG. III shows wave guide 4 and ultrasonic transducer 19 assembled and wave guide 4 is inserted into rigid or semi-rigid hollow tube 13 attached to handle 14. Irrigation is connected from source 25 to tubing 24 and controlled by valve 18. Seal 15, as shown in FIG. IV, prevents irrigation fluid flow around the proximal end of wave guide 4. Ultrasonic motor or transducer 19 is connected to ultrasonic generator 22 through cable 20. Fiber optic cable 7 is attached to light source 23. The assembly shown in FIG. III is then inserted into the proximal end 6 of flexible ureteroscope 5 and extended to the site of stone 3, as detailed in FIG. IV. Trigger 21 advances the tip of wave guide 4 to contact stone 3 and irrigation is turned on at valve 18. Ultrasonic transducer 19 is activated to cause wave guide to act on stone 3 with transverse and longitudinal motion of the end of wave guide 4 to machine away or disintegrate stone 3. Irrigation line 24 may be connected to a suction pump to remove disintegrated stone segments.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. An apparatus for machining and fragmenting urinary calculi in place and in a ureter, comprising a flexible ureteroscope, adapted to be inserted in a flexible state into said ureter to abut said urinary calculi to be fragmented, said ureteroscope having at least two substantially parallel lumens extending through said ureteroscope, an optical system in one of said lumens permitting optical observations lengthwise trough said ureteroscope, a solid wave guide extending lengthwise through another of said lumens of said ureteroscope, said solid wave guide having a lateral dimension less than the interior lateral dimension of said other lumen, ultrasonic means in operative relation to said wave guide and acting on said wave guide at one end to cause vibration at the other end, said optical system including a plurality of optical fibers forming an optical bundle and at least a part of said optical fibers being connected to a viewing means, the remaining optical fibers being connected to a light source.

2. The apparatus recited in claim 1 wherein an relatively rigid member is adapted to be introduced into said lumens, after said ureteroscope has been advanced into position in said ureter thereby straightening said flexible ureteroscope and ureter simultaneously whereby a physician is allowed to easily insert said ureteroscope in said ureter and then stiffen said ureteroscope with said relatively rigid tube after insertion of said ureteroscope into said ureter, the introduction of said relatively rigid member into said ureteroscope during the introduction being adapted to aid steerability of said ureteroscope.

3. The apparatus recited in claim 2 wherein said wave guide extends through said relatively rigid tube and said ureteroscope is straightened by said relatively rigid tube and said wave guide extends through said relatively rigid tube thereby substantially reduces friction zones between said wave guide and said tube thus reducing loss of ultrasonic vibration energy at the distal end of said wave guide.

4. The apparatus recited in claim 3 wherein said wave guide is a solid wire that has lateral dimensions proportioned to allow both transverse and longitudinal motion of said wave guide in said ureteroscope with optimum wire performance and wire life.

5. The apparatus recited in claim 2 wherein an irrigation means is connected to one of said lumens whereby fluid may be introduced into said one lumen of said ureteroscope whereby said lumen may be irrigated with said fluid during machining of said stone.

6. The apparatus recited in claim 2 wherein said elongated relatively rigid member is hollow.

7. The apparatus recited in claim 2 wherein said elongated relatively rigid member is hollow and semi-rigid.

8. A method of disintegrating urinary calculi under direct vision in a ureter comprising the steps of:
  (a) placing a relatively flexible ureteroscope in said ureter;
  (b) placing an elongated relatively rigid member said ureteroscope to straighten said ureteroscope;
  (c) placing a wave guide wire through said ureteroscope with one end of said wave guide wire abutting said calculi and the other end of said wave guide wire extending out of the opposite end of said ureteroscope;
  (d) subjecting said wave guide wire to ultrasonic vibrations whereby the end of said wave guide wire abutting said calculi is caused to vibrate while being observed through an optical system in a passageway in said ureteroscope.

9. The method recited in claim 8 wherein an optical system is disposed in said ureteroscope and including the steps of:
  (a) moving said wave guide wire both laterally and axially in said ureteroscope under optical observation to cause said calculi to be machined and fragmented;
  said optical system consisting of a plurality of optical fibers forming at least one cable.

10. The method recited in claim 9 wherein a guide wire is inserted into said ureter to the position of said calculi prior to inserting said ureteroscope and, relatively rigid member.
  said guide wire is removed before inserting said relatively rigid member.

11. The method recited in claim 9 wherein said optical fibers are divided into two bundles,
  said method includes attaching one said bundle to a light source and illuminating said calculi thereby and attaching the other said bundle to a viewing means and observing said calculi therethrough.

12. The method recited in claim 11 wherein irrigation fluid is introduced into said ureteroscope while said calculi is being disintegrated, whereby said calculi is irrigated with said fluid during machining of said calculi, wherein said disintegrated calculi is removed.

13. The method recited in claim 12 wherein said relatively rigid elongated member is hollow,
  said wave guide wire is passed through said hollow relatively rigid elongated member.

14. The method recited in claim 13 wherein said ureteroscope has a lumen and said relatively rigid member is passed through said lumen and said lumen has a lateral dimension substantially greater than the lateral dimension of said wave guide whereby said wave guide can be moved laterally relative to said ureteroscope.

15. The method recited in claim 13 wherein said ureteroscope comprises a plurality of passageways passing through said ureteroscope and said relatively rigid elongated member through one said passageway and said optical system passes through at least one other said passageway.

* * * * *